United States Patent [19]

Tanabe et al.

[11] Patent Number: 4,734,097

[45] Date of Patent: * Mar. 29, 1988

[54] MEDICAL MATERIAL OF POLYVINYL ALCOHOL AND PROCESS OF MAKING

[75] Inventors: Tatsuzo Tanabe, Sapporo; Masao Nambu, Yokohama, both of Japan

[73] Assignee: Nippon Oil Company, Ltd., Tokyo, Japan

[*] Notice: The portion of the term of this patent subsequent to Sep. 18, 2001 has been disclaimed.

[21] Appl. No.: 716,840

[22] Filed: Mar. 28, 1985

Related U.S. Application Data

[63] Continuation of Ser. No. 421,913, Sep. 23, 1982, abandoned.

[30] Foreign Application Priority Data

Sep. 25, 1981 [JP] Japan .................. 56-150549
Oct. 8, 1981 [JP] Japan .................. 56-159506

[51] Int. Cl.$^4$ ............................. B29C 35/16
[52] U.S. Cl. ........................ 623/11; 264/28; 523/309; 524/557; 528/481
[58] Field of Search ............ 264/28, 185, 343; 523/309; 524/557; 528/481; 623/11

[56] References Cited

U.S. PATENT DOCUMENTS 4,472,542 9/1984 Nambu .................. 523/309
4,524,064 6/1985 Nambu .................. 424/81

FOREIGN PATENT DOCUMENTS 52-1134 1/1977 Japan .................. 264/28
52-8071 1/1977 Japan .................. 264/28
55-71532 5/1980 Japan .................. 264/28
742900 1/1956 United Kingdom .

OTHER PUBLICATIONS

Peppas & Merrill, "Development of Semicrystalline Poly(vinyl Alcohol) Hydrogels for Biomedical Applications" J. Biomedical Materials Research, vol. 11, May 1977, pp. 423-434.
Bruck, "Aspects of Three Types of Hydrogels for Biomedical Applications" J. Biomedical Materials Research, vol. 7, Sep. 1973 pp. 387-404.
Lewis, "The Augmentation Mammaplasty" Plastic & Reconstructive Surgery, vol. 35, 1965 pp. 51-58.
Singh et al., "Polymeric Hydrogels: Preparation & Biomedical Applications" J. Scientific & Industrial Research, vol. 39, Mar. 1980, pp. 162-171.
Takahashi et al. "The Melting Temperature of a Thermally Reversible Gel. III Poly(Vinyl Alcohol)—Water Gels" Polymer J., vol. 6, pp. 103-107, 1974.
Tesoro, "Cross-Linking of Cellulose with Polyfunctional Sulfones Under Anhydrous Conditions," Textile Research J., Mar. 1962, pp. 189-201.
Drost-Hansen, "Role of Water Structure in Cell-Wall Interactions," Federation Proceedings, vol. 30, Sept.-Oct. 1971 pp. 1539-1548
Marvel & Denoon, "The Structure of Vinyl Polymers II Polyvinyl Alcohol".
Reimschuessel, "Structural Studies of Organic Gels by SEM" J. Materials Science, 1974, pp. 1815-1822.
Andrade et al., "Water as a Biomaterial" Transactions American Society for Artificial Internal Organs, vol. 19, 1973 pp. 1-7.

*Primary Examiner*—Jan H. Silbaugh
*Assistant Examiner*—Mary Lynn Fertig
*Attorney, Agent, or Firm*—Scully, Scott, Murphy & Presser

[57] ABSTRACT

Provided is a medical material comprising a molded hydrogel obtained by pouring an aqueous solution containing not less than 6 wt. % of a polyvinyl alcohol which has a degree of hydrolysis not less than 97 mole % and average polymerization degree not less than 1,100, into a desired shape of a vessel or mold, freeze-molding the aqueous solution at a temperature lower than −5° C., then partially dehydrating the resulting molded product without thawing it up to a percentage dehydration not less 5 wt. %, and if required, immersing the partially dehydrated, molded product in water to attain a water content thereof in the range of 45 to 95 wt. %.

11 Claims, No Drawings

MEDICAL MATERIAL OF POLYVINYL ALCOHOL AND PROCESS OF MAKING

This is a continuation of copending application Ser. No. 421,913, filed on Sept. 23, 1982, now abandoned.

BACKGROUND OF THE INVENTION

The present invention relates to a novel artificial medical material and more particularly to a medical material which comprises a hydrogel having superior properties not found in conventional natural or synthetic polymers.

In most of the tissues of a living body there is embedded a large amount of water, and it is as already often pointed out that this water has a very important significance [see Tatsuro Yamaguchi, "Ohyo Biseibutsu Kenkyu Seminar 1," Gihodo, p. 55 (1979); Hisashi Uedaira, Hyomen, 13, 297 (1975); W. Drost-Hansen, Federation Proc., 30, 1539 (1971); and J. D. Andrade et al., Trans. Am. Soc. Artif. Intern. Organs, 19, 1 (1973)].

Therefore, in the selection of prosthesis, a hydrous high polymer (hydrogel) is now expected to be superior in biocompatibility [see Tatsuzo Tanabe et al., "Jinko Kekkan," Nankodo, p. 56 (1977) and S. D. Bruck, J. Biomed. Mater. Res., 7, 387 (1973)].

Furthermore, in the case of using synthetic or natural high polymers as medical materials, thrombosis on the contact surface between those materials and blood has long been recognized as a serious problem of artificial valve, vascular graft, artificial kidney, liver, pancreas and catheter, and efforts have been continued for obtaining a material which is difficult to behave as a foreign body against blood, that is, a material which is difficult to form thrombus caused by blood destruction [see Tatsuzo Tanabe, Gekashinryo, 8, 1441 (1966) and Tatsuzo Tanabe et al., Jinko Zoki, 1, 17 (1972)].

A hydrogel does less damage to the tissues and an increase in its water content results in improvement in its antithrombosis, therefore it is expected as a medical material. However, all of conventional hydrogels have a serious defect such that they are inferior in mechanical strength. For this reason, their use is extremely limited [see Tatsuzo Tanabe et al., "Jinko Kekkan," Nankodo, p. 56 (1977); Tatsuzo Tanabe, Jinko Zoki, 5, 245 (1976); S. D. Bruck, J. Biomed. Mater. Res., 7, 387 (1973); H. Singh et al., J. Sci. Ind. Res., 39, March, 162 (1980); and J. D. Andrade et al., Trans. Am. Soc. Artif. Intern. Organs, 19, 1 (1973)].

There have been proposed a number of hardening means (for improving mechanical strength) involving treating a hydrogel (or gelling component) with formaldehyde, glutaraldehyde, terephthalaldehyde, or hexamethylenediamine. However, it is well known that since those treatments employ the chemicals harmful to tissue, thus treated hydrogel causes various troubles. For example, a vascular graft (Ivalon), obtained by cross-linking polyvinyl alcohol with formalin, has been broken. Moreover it has been pointed out that if such cross-linked product of a polyvinyl alcohol with formalin is used for augmentation mammoplasty, it contracts enormously. At present, it is considered that those chemicals cannot be used [see Tatsuzo Tanabe et al., "Jinko Zoki Shiryo Shusei," Life Science Center, p. 330 and 88 (1976); J. R. Lewis, Plast. & Reconstr. Surg., 35, 51 (1965); and Yasuo Muto, Nippon Rinsho Geka-Shi, 26, 25 (1965)].

Moreover, as a result of application of such chemical treatment, the superior characteristics of hydrogel and largely diminished.

As the sole method for hardening a weak hydrogel without application of such chemical treatment, irradiation method is now suggested [see N. A. Peppas et al., J. Biomed. Mater. Res., 4, 423 (1977) and H. Singh et al., J. Sci. Ind. Res., 39, (March), 162 (1980)]. But this method requires a special equipment and its effect is not so remarkable. Therefore, its practical application is difficult. Besides, there have been reported many examples wherein the superior features of a hydrogel are lost during radiation.

The present invention provides a prosthesis that is superior in mechanical strength and biocompatibility, prepared without the foregoing chemical treatment or irradiation.

The present invention further provides a thromboresistant material, which is obtained by embedding a medicine (anticoagulant) in the hydrogel of the present invention to improve the antithrombosis.

As the method of preventing the coagulation of blood by using a medicine, there has long been adopted a method wherein heparin (heparin calcium, heparin sodium, or the like) is administered by intravenous, subcutaneous or intramuscular injection, or a oral adminstration of Warfarin potassium (3-$\alpha$-phenyl-$\beta$-acetyl-ethyl-4-hydroxycoumarin potassium), Bishydrocoumarin (Dicumarol), Indan-1,3-dione, Ethylbiscoumacetate (Tromexan), Phenprocoumon (Liquamar), Acenocoumarin (Sintrom), Phenindione (Danilone, Dindevan, Hedulin), Diphenadione (Dipaxin), Anisindione (Miradon), or the like. However, the administration to an allergic subject for a long period is likely to cause asthma, urticaria, skin itching, rhinitis, epiphora, pyrexia, alopecia, spontaneous fracture, polyporous bone, hematoma with topalgia, interdental bleeding, epistases, vomiting and diarrhea. In general, moreover, the patient continues to encounter the dangerous hemorrhagic diathesis. Therefore, those methods are by no means preferable.

On the basis of the idea that it is not necessary to spread anticoagulant in whole cardiovascular system, there have been proposed many attempts to let a very small amount of anticoagulant be present on the surface of the medical material. For example, an anticoagulant (heparin, hirudin, antithrombin), a blood platelet agglutination inhibitor (adenyl cyclase, prostaglandin E, methylxanthine), and a fibrinolytic activator (urokinase, streptokinase) are applied to the surface of the medical material, or adsorbed through an ionic functional group, or immobilized by covalent bond [see Tatsuzo Tanabe Jinko Zoki 5, 247 (1976) and Jinko Zoki, 1, 17 (1972)]. However, in the application or adsorption method, the anticoagulant, etc. easily comes off the said contact surface and therefore the available period is short [see Tatsuzo Tanabe, Kyobu Geka, 25, 347 (1972)]. In the covalent-bond method, the anticoagulant is often damaged during the chemical reaction, and the introduced functional group may cause tissue reaction; besides, the anticoagulant thus immobilized cannot function as expected. This method is not useful [see Tatsuzo Tanabe, "Jinko Kekkan," Nankodo, p. 73 and 57 (1977); Yoji Imai, Kobunshi, 21, 570 (1972); Yuichi Mori et al., Kobunshi, 22, 614 (1973); H. Tanzawa et al., Trans. Am. Soc. Artif. Intern. Organs, 19, 188 (1973); Hiroshi Tanzawa, Geka Shinryo, 20, 2 (1978); Shigeo Shimizu et al., Kagaku Keizai, 24, (2) 19 (1977); Yuichi Mori, "Jinko Zoki Shiryo Shusei," Life Science Center, p. 117 (1976); and Hiroshi Tanzawa, Kagaku Kogyo, 1260 (1974)].

In order to avoid such drawbacks, there has been reported an attempt of embedding the anticoagulant into the medical material [see H. Tanzawa et al., Trans. Am. Soc. Artif. Intern. Organs, 19, 188 (1973)]. But it is often pointed out that the anticoagulant which has not been immobilized (entrapped) by means of any chemical bond is released, and the available period is considered to be 5 to 8 hours, or 5 days or so at most. With a view to decreasing the release (flow-out) rate of the anticoagulant, it has also been tried to chemically treat the surface of the material (or anticoagulant) with glutaraldehyde. In this case, however, it is necessary to take care not to damage the anticoagulant, for example, the treatment must be conducted at a pH of 4 to 5.5 and at a reaction temperature of 59° to 85° C. Therefore, it is impossible to expect much of the effect of the treatment.

The present invention dispenses with the operation using chemical reagents or radiation as in the conventional methods and hence does not damage at all the anticoagulant used, and embeds the anticoagulant firmly in a medical hydrogel, thereby providing a medical material capable of releasing the anticoagulant over a long period on the portion requiring an anticoagulating action (the contact surface between the medical material and blood).

The present invention uses a polyvinyl alcohol as a material for preparing an antithrombotic hydrogel. As the method of gelling an aqueous polyvinyl alcohol, there have already been proposed various methods. But, as summarized below, all of those methods are not satisfactory.

(1) By air-drying an aqueous polyvinyl alcohol solution, there is obtained a wet or dry film, which, however, is merely a weak film inferior in water resistance and having no stiffness in water and applied to only limited uses (see Japanese Patent Publication No. 9523/1965).

(2) Also by the method herein an acid is added to an aqueous suspension containing polyvinyl alcohol and tetraethyl silicate, followed by air-drying, there merely is obtained a similar film to that obtained in the above (1). In this connection, there has also been proposed the application of freeze-drying after addition of the acid; but the film thereby obtained is rather deteriorated in its strength to the extent that the molding operation for the film is scarcely feasible (see Japanese Patent Publications Nos. 30358/1980 and 11311/1980).

(3) It is well known that an aqueous polyvinyl alcohol solution forms a gel during cobalt 60 (γ-ray) radiation. In this case, however, special facilities (irradiation facilities) are absolutely necessary and the irradiation cost is high; besides, the resultant gel is weak and often requires another hardening (secondary hardening treatment). Therefore, the gel obtained by this method is difficult to be utilized except in special uses where a highly viscous liquid (or a soft gel) is desired, such as an artificial vitreous (intraeyeball filling liquid) (see J. Material Sci., 1974, 1815 and Japanese Patent Laying Open Print No. 55647/1975).

(4) Also, it has long been well known that an aqueous polyvinyl alcohol, when mixed with boric acid (or an aqueous solution thereof) or borax (or an aqueous solution thereof) (Note: borax=sodium tetraborate decahydrate), gels immediately. But the gel thus obtained is weak, has fluidity, and is torn to pieces immediately when merely picked with finger tips; therefore, its shape is difficult to be retained [see J. Am. Chem. Soc., 60, 1045 (1938) and French Pat. No. 743942 (1933)]. Besides, this borax gel easily collapses at a pH value not higher than 8 though it can exist under an alkaline condition, and therefore it is difficult to utilize it as a medical material, and thus it is of little value.

(5) There also have been proposed a number of gelling methods for polyvinyl alcohol by using phenols such as phenol, naphthol and Congo Red or amino compounds or metallic compounds such as titanium, chromium and zirconium, but all of which involve the same drawbacks as in the above (4) (see Nippon Kagaku Zasshi, 72, 1058 (1951) and Japanese Patent Publication No. 9523/1965 and No. 23204/1965).

(6) Also well known is the gelation of polyvinyl alcohol by using cross-linking agents or copolymer components such as aldehydes, dialdehydes, unsaturated nitriles, diisocyanates, trimethylolmelamine, epichlorohydrin, bis-(β-hydroxyethyl)sulfone, polyacrylic acid, dimethylolurea and maleic anhydride; however, these methods require chemical reagents and a strong gel having a high water content is not obtainable [see Textile Res. J., (3), 189 (1962) and British Pat. No. 742,900 (1958)].

(7) Aqueous polyvinyl alcohols are known to form hydrogels by allowing them to stand at a low temperature not higher than 40° C., particularly beween 0° C. and 18° C. [see Kominami et al., Kobunshi Kagaku, 12, 218 (1955); Maeda et al., Kobunshi Kagaku, 13, 193 (1956) and Kogyo Kagaku Zasshi, 59, 809 (1956)]. However, the gel formed at room temperature is fragile like agar and carrageenan, and it dissolves by vigorous stirring, mixing with water or warming [see Kominami et al., Kobunshi Kagaku, 12, 218 (1955) and Takahashi and Sakurada, Kobunshi Kagaku, 13, 502 (1956)]. It is also well well known that low temperatures are desirable for obtaining polyvinyl alcohol gels, and there are known examples wherein the gelation is carried out at low temperatures of 18° C. and further 0° C. or even at a temperature below 0° C. [see Maeda et al., Kobunshi Kagaku, 13, 193 (1956), Japanese Patent Publication No. 12854/1972 and Takahashi et al., Polymer J., 6, 103 (1974)]. In any case, however, the resultant gel is weak (or a viscous liquid) like ager, carrageenan and jelly, is very sticky and poor in water resistance, swells remarkably in water and softens, is partially dissolved out into water and the remainder becomes paste-like. Moreover, in warm water at 40°–50° C., the gel easily gets out of shape and is dispersed and dissolved in water. Thus, it is difficult to recognize its value as a medical material.

(8) A spongy product obtained by formalizing a polyvinyl alcohol has also been well known, but it is not stable within a tissue, and along with its decomposition and deterioration, it exerts a harmful influence upon its surroundings. In recent years, therefore, its use has been extremely limited [see Tatsuzo Tanabe et al., "Jinko Zoki Shiryo Shusei," Life Science Center, p. 330 (1976); ibid. p. 88 (1976); and J. R. Lewis, Plast, & Reconstr. Surg., 35, 51 (1965)].

(9) Also known is a method wherein a small amount of a polyvinyl alcohol is added to an aqueous solution of a water-soluble high polymer having gelling ability such as agarose, agar, albumin, alginate, curdlan, carrageenan, casein, CMC (sodium carboxymethyl cellulose), furcellaran, gelatin, methyl cellulose, pectin, starch, tamarind gum, xanthan gum, tragacanth gum, or guar gum, and the resulting solution is allowed to cool or immersed in a gelling agent-containing bath (coagulation bath) or subjected to freeze-drying [see Fragrance Journal, 2, (7) 68 (1974) and Japanese Patent Publications Nos. 25210/1981 and 25211/1981]. Even according to this method, there merely is obtained a weak and water-soluble viscous liquid or dry water-soluble powder (freeze-dried powder).

SUMMARY OF THE INVENTION

It is an object of the present invention to eliminate the foregoing drawbacks associated with the prior art.

It is another object of the present invention to provide a medical material which comprises a water-insoluble gel having a high water content and being superior in elasticity, mechanical strength and biocompatibility.

Other objects and advantages of the present invention will become apparent from the following description.

According to the present invention, there is obtained a medical material comprising a hydrogel obtained by pouring an aqueous solution which contains not less than 6 wt.% of a polyvinyl alcohol having a degree of hydrolysis not less than 97 mole% and a viscosity-average polymerization degree not less than 1,100, into a desired shape of a vessel or mold, then freeze-molding the aqueous solution at a temperature lower than −5° C., thereafter partially dehydrating the molded product without thawing it up to a percentage dehydration not less than 5 wt.% (percentage loss in weight of the frozen body), and if required, immersing the dehydrated product in water until its water content is in the range of 45 to 93 wt.% (on a wet body basis).

Thus, in the present invention, the aqueous polyvinyl alcohol is freeze-molded and then subjected to vacuum-partial dehydration, whereby there is obtained a desire shape of gel having a high water content and being superior in mechanical strength. In the gelling step and its pretreatment step, the present invention does not employ at all an acid, an alkali, a radical source, radiation, an organic solvent, a reagent or an inorganic solvent except water, though those have heretofore been used commonly in the gelation of synthetic high polymers, nor does it require a secondary hardening treatment (post-treatment). Besides, the gel obtained in the present invention has a high water content and has a rubbery elasticity and a superior mechanical strength. Furthermore, the gel of the present invention is insoluble in water or warm water and does not exhibit any stickiness, and also in this point it is entirely different from the foregoing cooled gel of an aqueous polyvinyl alcohol solution. That is, the present invention provides a novel gel in a manner quite different from the conventional knowledge on gelation involving allowing to cool or chemical treatment of an aqueous polyvinyl alcohol solution.

DETAILED DESCRIPTION OF THE PREFERRED EMBODIMENTS

Polyvinyl alcohols which may be used in the present invention are required to have a degree of hydrolysis not less than 97 mole%, preferably not less than 98 mole%. Even if there is used a polyvinyl alcohol having a degree of hydrolysis ranging from 80 to 88 mole%, particularly not more than 85 mole%, there merely is obtained a weak gel, and the objects of the present invention are not attained.

Furthermore, polyvinyl alcohols which may be used in the invention are required to have an average degree of polymerization not less than 1,100, preferably not less than 1,800. If their polymerization degree is in the range of 300 to 500, there merely is obtained a viscous liquid or a weak gel. For example, polyvinyl alcohols having a degree of polymerization in the range of 1,100 to 3,300, preferably 1,800 to 3,300, may be used in the present invention, and preferably, commercially available ones of a high polymerization degree (1,800–2,600) are used as they are.

According to the present invention, first an aqueous solution containing not less then 6 wt.% of polyvinyl alcohol is prepared. Therefore, the polyvinyl alcohol concentration may be set, for example, in the range of 6 to 25 wt.%, more preferably 6 to 15 wt.%. It may be raised up to about 50 or more, but in this case, the viscosity of the aqueous solution at room temperature reaches as high as 10,000 cP or more, or an increase in viscosity or gelation may occur during storage, thus making its handling somewhat difficult. The polyvinyl alcohol concentration may be set, for example, at 5 wt.% or lower, but in this case the time required for dehydration as will be described later becomes longer, thus resulting in increase of the cost (cost of dehydration power).

The aqueous polyvinyl alcohol solution thus prepared is then sterilized, for example, by steam at a high pressure and poured into a pre-sterilized, desired shape of a vessel or mold, then freeze-molded. More specifically, the aqueous polyvinyl alcohol solution is cooled to a temperature lower than −5° C. by using as a cooling agent, for example, a freezing mixture such as common salt—ice (23:77, −21° C.) or calcium chloride—ice (30:70, −55° C.), or dry ice—methyl alcohol (−72° C.), or liquid nitrogen (−196° C.), and it is thereby frozen. Insufficient cooling is not preferable in the present invention, because the shape of the gel obtained after going through a partial dehydration step as will be described later does not coincide with the expected shape or the shape of the vessel or mold into which the aqueous polyvinyl alcohol has ben poured, and also because the mechanical strength of the gel is inferior. The use of liquid helium permits cooling down to −269° C., but it is not economical, nor is it advantageous to the quality of the gel. Practically, it is preferable that the cooling be done to, for example, −20° to −80° C. by using a Freon refrigerator. The cooling temperature affects the strength of the gel obtained after going through a partial dehydration step as will be described later. In case it is desired to obtain a gel having a specially strong rubbery elasticity, the cooling temperature should be not higher than −5° C., preferably it is in the range of −15° to −55° C.

If the freeze-dehydration step is omitted, the waterresistant hydrogel of a high water content having a rubbery elasticity of the present invention is not obtainable.

In the freeze-dehydration step in the present invention, the cooling may be performed either slowly at a rate of 0.1 to 7° C. per minute or rapidly at a rate of 7° to 1,000° C. per minute. And in this step, the aqueous polyvinyl alcohol is solidified (frozen) in a desired shape of a vessel or mold. After making sure that the aqueous polyvinyl alcohol solution poured into such vessel or mold was frozen, the frozen body is subjected to vacuum-dehydration without thawing it and while retaining its shape, and if required after removing the upper or lower cover (or both) of the mold. In this case, if the freeze-molded product after taking out of the refrigerating chamber is transferred into a vacuum-dehydration chamber and immediately dehydrated by suction, the sample is cooled along with removal (sublimation) of water, therefore it will never thaw even without special application of an external cooling. Heating may be applied to the freeze-molded product to the extent that it does not thaw, whereby dehydration can be accelerated. That is, the temperature in the dehydration step is not specially limited as long as the freeze-molded product does not thaw, and it has no special influence upon the quality of the gel. The vacuum dehydration as referred to herein means a dehydration under reduced pressure. The degree of pressure reduction is not specially limited, but, for example, the dehydration may be carried out at a pressure not higher than 1 mmHg and preferably not higher than 0.1 mmHg.

Thus, in the present invention, the freeze-molded product is subjected to partial dehydration treatment regardless of the concentration of the aqueous polyvinyl alcohol solution. The percentage dehydration in this dehydration step should be not less than 5 wt.%, preferably not less than 10 wt.%. For example 5–90 wt.% is adopted.

As the dehydration proceeds, the strength of the gel is remarkably enhanced and properties such as non-stickiness and water resistance are improved to a remarkable extent, and thus this partial dehydration treatment is indispensable to the present invention. But in the present invention it is not necessary to carry out the dehydration (drying) treatment to such an extent as in the freeze-drying of intravenous injection drugs or of hydrous foods such as coffee, milk, fruit juice and noodles. The objects of the present invention can be fully attained by the above-mentioned partial dehydration treatment. And as mentioned above, since the strength of the gel is remarkably enhanced along with advancement of the dehydration, the percentage dehydration can be selected according to the desired strength of the gel. In any case, this freeze-partial dehydration treatment is indispensable to the present invention and has a very important significance. Its omission, therefore, would never afford the hydrogel of the present invention which is non-fluid and non-sticky, has a high water content and is superior in mechanical strength.

The freeze-molded and -partially dehydrated product is then thawed, for example, by allowing it to stand at room temperature, whereby there is obtained a gel rich in elasticity. The thawing may be carried out either slowly at a rate of 1° to 3° C. per minute or rapidly at a rate of 3° to 1,000° C. per minute. A rapid thawing using warm water or warm air may be applied. But the gel of the present invention is dissolved in hot water, and at a temperature above 60° C. a hard film is rapidly formed on its surface. Therefore, a high-temperature thawing must be avoided, and it is desirable that the thawing be done at a temperature of 40° to 50° C. or lower.

After the thawing operation, the gel can be removed easily from the support portion of the vessel or mold. Then, it absorbs water in a sterilized water or sterilized physiological saline and its water content reaches 45 to 93 wt.% (on a wet body basis) in 1 to 6 hours, but it is still a strong elastic body. Although the final water content ranges from 45 to 95 wt.%, an optimum value may be selected according to uses. For example, in case the gel is to be used for mammary augmentation, it is preferable that its water content be in the range of 90 to 95 wt.%. Although the water content of the gel is not so high as that devil's tongue jelly (a polysaccharide wet gel; water content about 97 wt.%), it is similar to the water content (70–90 wt.%) of bean curds, jelly, tissue cells. Besides, in point of strength and elasticity, it is far superior to polysaccharide gels such as devil's tongue jelly, agar, alginic acid, carrageenan, guar gum, locust been gum and agarose and protein gels such as bean curds and jelly, and it is rather similar to the muscle of human beings and animals. Despite of such a high water content, the gel of the present invention exhibits a strong elasticity, and when gripped strongly, it is deformed temporarily, but immediately reverts to its original shape, and thus it does not get out of shape. Furthermore, even if an adult stands on a plate-gel having a water content of 88% prepared according to the present invention with his one or both legs, the gel, though it is deformed temporarily, reverts to its original shape as soon as the stress is removed and does not get out of shape.

High water content and mechanical strength have heretofore been considered incompatible with each other in synthetic medical materials, but the gel of the present invention has the foregoing high water content and strength and it is a novel gel entirely different from the conventional film obtained by air-drying an aqueous polyvinyl solution or the foregoing adhesive and water-soluble gel obtained when aqueous polyvinyl alcohol is merely stored at 0° to 30° C. or lower.

Even if pressure is applied to the gel of the present invention, the water contained therein little exudes. For example, in case the gel of the present invention contains 90 wt.% of water, application thereto of a compressive stress of 4 kg/cm$^2$ causes only 1 to 2% of the water contained therein to exude. Thus, the gel of the present invention retains water firmly, from which it is apparent that the apparent specific gravity of the gel is almost the same as that of water and the gel barely precipitates in water.

The gel of the present invention has no stickiness and is water-insoluble. Even when about 10 g. of the gel which has been molded in the form of a plate (8 mm × 8 mm × 2 mm), a cylinder (inside dia. 3 mm, outside dia. 6 mm, length 6 mm), and a sphere (4 mm dia.), is stirred in 50 ml. of a sterilized water for 40 days, there are not recognized at all such phenomena as mutual adhesion and getting out of shape. When the gel was immersed in a physiological saline for one year, it did not dissolve therein nor did it change in its elasticity and strength (this is in marked contrast to the case of, for example, devil's tongue jelly which when immersed in tap water for several days gets out of shape severely, and also to the case of a mere cooled gel of aqueous polyvinyl alcohol which exhibits a remarkable stickiness and is often in the form of a viscous liquid or jelly, pudding or agar at best, and which is easily dispersed and dissolved in water).

In the present invention, polyvinyl alcohol is used as gelling component. However, inorganic or organic substances which do not impede the gelation of polyvinyl alcohol may be co-existent, for example, in an amount of one half or less of the amount of the polyvinyl alcohol. On the other hand, substances which act on polyvinyl alcohol (or polyvinyl acetal, polyvinyl butyral, or the like as a modified polyvinyl alcohol) to form a composite gel, and substances which react with polyvinyl alcohol to change the quality of the latter, even in a small amount, often badly affect the gel formation (formation of gel from a single polyvinyl alcohol cmponent) in the present invention and make it difficult to obtain a gel of a high water content superior in mechanical strength. Examples of such substances include those whose interaction with polyvinyl alcohols is already known, such as colloidal alkali silicate [see U.S. Pat. No. 2,833,661 (1958)], colloidal silica [U.S. Pat. No. 2,833,661 (1958)], alkaline colloidal silica (Japanese Patent Laying Open Print No. 153779/1979), organic silicon compounds ["polyvinyl acetate", Nikkan Kogyo Shinbunsha p. 93 (1963)], tetraalkyl silicate (Japanese Patent Publications Nos. 30358/1980 and 11311/1980), boric acid and borax [French Pat. No. 743942 (1933)], phenol, naphthol, m-cresol, pyroggllol, salicylanilide, disalicylbenzidide, resorcinol and polyamines [Kobunshi Kagaku, 11 (105 23 (1954)], and kaolin [Nature, 170, 461 (1955)]. The use of these substances should be avoided because they would form inconvenient weak composite gels with polyvinyl alcohols according to their co-existent amounts.

Examples of the foregoing inorganic or organic substances which do not impede the gelation of polyvinyl alcohol include active carbon, zeolites, anticoagulant as will be described later [heparin (sodium salt or calcium salt)], propylene glycol, glycerin, enzymes, and various medicines. In the case of using propylene glycol and glycerin, the concentration of poylvinyl alcohol in the aqueous polyvinyl alcohol solution can be decreased to less than 6 wt.%, for example, to 4–6 wt.%.

The appearance (color) of the gel of the present invention closely resembles that of slices of raw squid, rice cake, sweet rice jelly (white), boiled fish cake, and fresh fish (white flesh).

The sense of touch of the gel of the present invention is similar to that of human and animal flesh, slices of raw squid, fish meat, rice cake, fish stick, minced and steamed fish, shao-mai, and sausage.

The shape of the vessel or mold into which is to be poured the aqueous polyvinyl alcohol may be selected optionally to obtain a wet gel of a desired shape (granules, film, lump, plate, cylinder, or any other shape). The gel may be molded to match the shape of the final object product, or may be once molded and then formed into another shape by cutting or other means.

The gel of the present invention even when compressed strongly allows little water contained therein to exude, but upon air-drying it contracts while losing water gradually and stiffens remarkably. Besides, thereafter, even when immersed again in cold water, it never reverts to its original state of high water content although it somewhat absorbs water and swells (these phenomena resemble the cases of animal muscle, fish meat, squid and persimmon). In water or physiological saline, however, the gel of the present invention retains its initial fresh appearance and touch, and in intracorporeal circumstances, it does not undergo air-drying, dehydration, contraction and stiffening.

The gel of the present invention imbibes a large amount of water. By immersing it in water or physiological saline for 1 to 16 hours, its water content easily reaches 50 to 92 wt.%. Particularly, by setting the concentration of polyvinyl alcohol in the starting aqueous solution thereof at 6–20 wt.%, subjecting the aqueous polyvinyl alcohol solution of freeze-molding-partial dehydration and then immersing the molded body in water or physiological saline, there is obtained a gel with a high water content reaching as high as 70 to 95 wt.%. That is, the highly hydrous gel of the present invention is a rubbery elastic body having a superior mechanical strength as previously noted, and yet, chemically and biochemically, it often behaves as if it were mere water (or physiological saline), and thus its tissue (foreign body reactivity) is extremely slight. Also against blood, it exhibits a superior antithrombosis. As an example, in the cases of glass, nylon, polystryene, polyester (Dacron), polyethylene and polyurethane foam, blood coagulates extremely easily [see "Jinko Zoki Shiryo Shusei," Life Science Center, p. 115 (1976)], and also in the cases of Teflon, silicone and polyvinyl pyrrolidone, there occurs blood coagulation, while the highly hydrous gel of the present invention still exhibits antithrombosis even under conditions under which thrombosis is recognized in polyvinyl pyrrolidone, silicone and Teflon.

The water content of the hydrogel which has heretofore been taken note of as a medical material, namely, poly(2-hydroxyethyl methacrylate), usually ranges from 38 to 40 wt.%, and this hydrogel is inferior in its mechanical strength [see Tatsuzo Tanabe, "Jinko Kekkan," Nankodo, p. 56 (1977); Jinko Zoki, 5, 245 (1976); Hiroshi Tanzawa, Kogyo Zairyo, 25, 70 (1977); Geka Shinryo, 20, (1) 3 (1978); S. D. Bruck, J. Biomed. Mater. Res., 7, 389 (1973); and Hiroshi Tanzawa, Kagaku Kogyo, 1258 (1974)]. It has been proposed to increase its water content up to about 60 wt.%, but the mechanical strength of the hydrogel is diminished with increase in its water content [see J. S. Andrade (ed.), "Hydrogels for Medical and Related Applications," ACS Symp. Ser. 31, p. 23 (1976) and Yuichi Mori, "Jinko Zoki Shiryo Shusei," Life Science Center, p. 116 (1976)].

On the other hand, in the present invention, a highly hydrous gel having a water content in the range of 45 to 95 wt.%, preferably 70 to 92 wt.% and more preferably 80 to 92 wt.% is easily obtainable and its mechanical strength is superior, and thus it has a value as a medical material superior to any of conventional hydrophobic and hydrophilic, hydrous medical materials.

The hydrogel of the present invention allows water and water-soluble low-molecular weight compounds such as ammonia, common salt, uric acid, urea, creatinine, glucose, lactic acid and antibiotics to pass therethrough, but inhibits the intrusion of bacteria, yeasts and molds. Therefore, even if the sterile hydrogel of the present invention should be handled non-aseptically, the contamination is limited to the surface of the hydrogel. Prior to its use, therefore, the hydrogel can be made again aseptic by sterilizing its surface by the application of ultraviolet ray or by using propylene oxide, ethylene oxide, ozone, hydrogen peroxide, formaldehyde, glutaraldehyde, ethyl alcohol (70–90%), isopropyl alcohol (30–50%), or chlorhexidine, followed by washing with clean water or physiological saline.

Although the hydrogel of the present invention has a high water content and exhibits a superior antithrombosis, it cannot always assure just the same behavior as that of the water or physiological saline [see Tatsuzo Tanabe, Rinsho Geka, 22, 13 (1968) and Tatsuzo Tanabe et al., Jinko Zoki, 1, 17 (1972)]. Indeed, there is an expectation that a highly hydrous gel will not be recognized as a foreign body against blood [see Yuichi Mori et al., Kobunshi, 22, 613 (1973); Hiroshi Tanzawa, Kagaku Kogyo, 1258 (1974); J. D. Andrade et al., Trans. Am. Soc. Artif. Intern. Organs, 19, 1 (1973); and Yuichi Mori, "Jinko Zoki Shiryo Shusei," Life Science Center, p. 116 (1976)], but there still remains opportunity for further study. The idea that an increase in the water content of a medical contributes to the improvement of antithrombosis, is not unreasonable [see A. S. Hoffmann et al., Trans. Am. Soc. Artif. Intern. Organs, 18, 14 (1972) and S. D. Bruck, J. Biomed. Mater. Res., 7, 391 (1973)], but as long as medical materials are premised, it is impossible to increase the water content infinitely. The hydrogel of the present invention can have a water content much higher than the upper limit value (60–80%) of water content of heretofore proposed polyvinyl alcohol-glutaraldehyde system of poly(2-hydroxyethyl methacrylate) gel [see E. W. Merrill et al., ACS Polymer Preprint, 13, 513 (1972) and J. D. Andrade (ed.), "Hydrogels for Med. & Related Applications," p. 23 (1976)]. But if its water content exceeds 95 wt.%, its mechanical strength becomes deteriorated.

With a view to ensuring a sufficient antithrombosis over a long period while maintaining the water content of the gel of the present invention in the range of 45 to 95 wt.%, an anticoagulant may be embedded in the gel. As such drug which may be used in the invenion, heparin (heparic acid, heparin sodium, heparin potassium, heparin calcium, heparin magnesium) is effective. In order to embed such antithrombotic agent in the antithrombotic, highly hydrous gel of the present invention and thereby ensure the antithrombosis of the gel over a long period, any of a pre-sterilized heparin powder, aqueous heparin or aqueous heparin suspension is added and mixed into the starting aqueous solution or pre-sterilized aqueous polyvinyl alcohol solution used in the present invention. In this case, for the sterilization of the aqueous polyvinyl alcohol solution, it is convenient to adopt the foregoing high-pressure steam sterilization method, but for the sterilization of heparin there may be adopted a sterilization method using ethylene oxide, glutaraldehyde, formalin, propylene oxide, or hydrogen peroxide, and in the case of an aqueous solution thereof, there also may be adopted a sterilization method by filtration using a sterile filter.

The concentration of polyvinyl alcohol and that of heparin in the so-prepared aqueous solution may be selected to be not lower than 6 wt.% and not higher than 10 wt.%, respectively. A larger amount of heparin may be added and partially suspended in the aqueous solution, but since the heparin once embedded in the hydrogel of the present invention is embedded (gradually released) over a long period without flowing out in a short period, it usually is not necessary to add a specially large amount of heparin into the aqueous polyvinyl alcohol.

The aqueous polyvinyl alcohol-heparin solution thus obtained is then subjected to the foregoing freeze-molding and partial dehydration, whereby not less than 99% of heparin in the aqueous solution can be dispersed and embedded uniformly in the gel. The heparin-embedded frozen body can be used as a medical material after thawing, or it may be immersed in a sterilized water or physiological saline for 1 to 16 hours to obtain a wet gel having a water content of 50 to 92 wt.% in a state close to an equilibrium water absorption, and this gel may be used in a stabilized shape. During this immersing operation, a small amount of heparin flows out of the hydrogel, but the flow-out loss is usually only about 0.5 to 1% of its total amount embedded, and the antithrombosis of the hydrogel of the present invention is not thereby affected. For example, in case heparin sodium is dissolved 3 wt.% in the aqueous polyvinyl alcohol followed by application of the process of the present invention and 5 g. of the resultant gel (total surface area: 50 cm$^2$, amount of heparin embedded; 4,800 units (30 mg)/g) is immersed in 5 ml. of physiological saline for 6 hours, the flow-out loss of heparin is about 0.6%, and even if it is contacted with the blood stream for at least 28 days, heparin is still present on the surface of the hydrogel.

In the case of heparin embedded in an aldehyde crosslinked gel of polyvinyl alcohol, it usually flows out in its total amount in 5 to 8 hours or in about 5 days at most. In view of this fact, it is apparent that the sustained releasing effect over a long period of the embedded heparin in the present invention is unique and very preferable as a medical material.

The gel of the present invention can be obtained easily as a molded product of a desired shape. For example, it can be formed into a hydrogel pipe or heparin-embedded hydrogel pipe having a diameter of 2 to 6 mm, and the pipe can be used as an vascular grafts. All of the presently available vascular graft (polyester or Teflon) exhibit thrombosis and are difficult to be used as a substitute for arteria 5 mm or less in diameter, and their application to the vena where the flowing velocity of blood is small, is also difficult. On the other hand, the hydrogel pipe or heparin-embedded hydrogel pipe of the present invention does not produce thrombus over a period of at least four weeks even when used as a substitute for arteria 2 to 5 mm in diameter or the vena, during which period protein adhers thinly throughout the surface of the pipe, and thus its biocompatibility is fully attained.

Furthermore, active carbon may be embedded in the gel of the present invention. As an adsorption type artificial kidney as a substitute for the present dialysis by Cuprophan, there has been proposed an attempt to coat active carbon with hydrogel such as gelatin or poly(2-hydroxyethyl methacrylate). The hydrogel or heparin-embedded hydrogel of the present invention, of course, can coat active carbon. Besides, its mechanical strength (abrasion resistance) and antithrombosis are superior to those of gelatin and poly(2-hydroxyethyl methacrylate), the hydrogel or heparin-embedded hydrogel of the present invention is a more desirable material in preventing leakage of active carbon and formation of thrombus. Moreover, the optionally heparin-embedded hydrogel of the present invention can be used as a material for artificial organs of which is required antithrombosis, such as shunt for artificial dialysis, artificial valve for the heart, and intraaorta balloon. Additionally, it is useful as a coating material for various catheters which are in contact with blood, such as an electrode for measuring blood oxygen concentration. Such hydrogel of the present invention can be used also as a coating on the surface of conventional medical materials such as Teflon, polyester, polyethylene, polyurethane, and polyurethane-dimethyl polysiloxane.

Likewise, the hydrogel of the present invention is employable as prosthesis, for example, for anaplasty of depression or orbita or eyelid, caused by operation for erysipelatous palpebra, empyema, osteomyelitis or ophthalmitis, or by burn or trauma, for plasty of depression of the chest and appendicular atrophy caused by infantile paralysis or trauma, for mammoplasty for amastia (amazia) caused by operation of mammary cancer, for cosmetic plasty for mammary augmentation anorchism caused by trauma, abdominal cryptorchism, tuberculosis of the epidymis, orchioncus and prostatic cancer, and further as a reconstructive material for the biliary tract, urethra, esophagus, tendon and oviduct.

In case the hydrogel of the present invention is implanted, it is encapsulated with a thin film of tissue in 3 to 4 weeks, but inflammation or cellular infiltration is not recognized, and any tissue does not intrude into the gel. Besides, by applying a knife to at least part of the capsula, the gel can be easily removed. This hydrogel can be used for mammary augmentation in the form of bag-prosthesis. In conformity with the shape of commercially available bag-prosthesis, the hydrogel of the present invention can be molded to 8 to 12 cm in diameter of the bottom (circular) and 80 to 450 ml. according to the capacity of the bags.

The bags after filling with the hydrogel of the present invention are sealed by a stopper attached thereto, or alternatively, the entrance may be ligated with suture.

The hydrogel of the present invention contracts and is deformed when subjected to a finger pressure, and reverts to its original shape upon removal of the external pressure. Therefore, the bag filled with this gel can be pushed in known manner from a 3–5 cm opening in the submammary sulcus into a lumen between glandula mammaria and musclus pectoralis major, and thereafter the incised opening can be sutured.

As a commercial bag, it is convenient to use a familiar silicone bag whose safety has been confirmed.

The hydrogel of the present invention is employable also as non-adhesive material. In this case, from the view point of pyostatics, a medicine may be embedded in the hydrogel. More specifically, a medicine can be embedded in the gel by adding medicine beforehand into the foregoing aqueous polyvinyl alcohol and then applying thereto the freeze-molding and vacuum dehydration process of the present invention.

It is convenient to perform the above adding procedure after sterilization of the aqueous polyvinyl alcohol, but in the case of a heat-resistant medicine, the medicine may be added beforehand into the above aqueous solution and then subjected to sterilization with steam under pressure followed by application of the foregoing gelling procedure in the present invention (freeze-molding and vacuum dehydration) in the same manner, whereby there is obtained an elastic material having superior adhesion preventing ability. Examples of medicines to be embedded in the gel include, from the standpoint of pyostatics, sulfadiazine, slver sulfadiazine, benzalkonium chloride, cetalkonium chloride, methylbenzethonium, neomycin sulfate, hexachlorophene, eosine, penicillin G, cephalothin, cephaloridine, tetracycline, lincomycin, nystatin, kanamycin, penicillinase-resistant penicillin, fradiomycin sulfate, and silver lactate. Among the antibacterial agents, for example, the solubility in water of sodium sulfadiazine is as high as 50 wt.%, but sulfadiazine dissolves only 1 g. in 13,000 ml. of water. In the present invention, however, it is not always necessary to use the antibiotics in the form of an aqueous solution. Powder or suspension may be added and mixed into the foregoing aqueous solution of polyvinyl alcohol, whereby they can be embedded in the gel of the present invention.

Barbital (5,5-diethylbarbituric acid) as hypnotics, (analgetics); Sulpyrin (1-phenyl-2,3-dimethyl-5-pyrazolon-4-methylaminomethansulfonic acid sodium salt), pentazocine (1,2,3,4,5,6-hexahydro-6,11-dimethyl-3-(3-methyl-2-butenyl)-2,6-methano-3-benzazocin-8-ol) and Azabicyclane (9$\beta$-methoxy-9$\alpha$-phenyl-3-methyl-3-azabicyclo [3.3] nonane citrate) as antipyretics, (analgetics, antiphlogistics); Pridinol methanesulfonate (1,1-diphenyl-3-piperidine propanol-1-methanesulfonate) and Methocarbamol (3-(0-methoxy-phenoxy)-2-hydroxypropyl-1-carbamate) as local anesthetics and muscle relaxants; and clauden and vitamin Ka (2-methyl-1,4-naphthoquinone) as styptics, may also be embedded and gradually released in the hydrogel of the present invention.

The medicines may be added into the aqueous polyvinyl alcohol in an amount not larger than 15 times the weight of the polyvinyl alcohol, for example 0.2–4 wt.% fradiomycin sulfate, 1–25 wt.% sulfadiazine and 0.2–1 wt.% penicillin G. The medicine once embedded in the gel of the present invention is kept embedded and gradually released over along time without flowing out in a short time. For example, in case sulfadiazine sodium is dissolved 3 wt.% in a mixed aqueous solution of polyvinyl alcohol and polyhydric alcohol followed application of the procedure of the present invention and 5 g. of the resultant gel is immersed in 5 ml. of physiological saline for 6 hours, the flow-out loss of the sulfadiazine sodium is about 30%, and thereafter, even if immersed in 5 ml. of a fresh physiological saline for 3 days, the release of the sulfadiazine is still continued, with 15% of the initially embedded amount thereof still remaining in the gel. Therefore, it is desirable to select the amount of each medicine to be embedded in accordance with doctor's instructions while taking into account the gradually releasing speed of the medicine and the object of therapy (or prophylaxis).

As set forth hereinabove, the hydrogel of the present invention, in addition to its use as various medical materials, is preferably used as a medical material to be applied to a portion inside or outside a living body where the material is brought into direct contact with blood.

The hydrogel of the present invention can also be coated on the surfaces of various conventional medical materials.

The reason why an antithrombotic gel rich in elasticity and superior in mechanical strength, quite different from conventional polyvinyl alcohol gels, can be obtained by freeze-molding and subsequent partial dehydration according to the present invention, is not clear, but it is presumed to be because during the freeze-molding and subsequent partial dehydration treatment there are formed a very large number of hydrogen bonds intra and inter the molecules of polyvinyl alcohol, and particularly by partial dehydration the degree of crystallization of the gel is enhanced, thereby improving mechanical strength and elasticity.

The following examples are given to further illustrate the present invention.

EXAMPLE 1

In 140 ml. of water were dissolved 23 g. of powdered (water content, 8.5% by weight) polyvinyl alcohol available on the market (saponification value, 99.4 mol%; average degree of polymerization, 2,600; viscosity (4%; aqueous solution), 66 cP) to give a 13% by weight aqueous solution. The solution was subjected to a steam sterilization treatment under pressure (120° C. × 20 min.).

Into a pipe mold 5 mm. in inner diameter, 10 mm. in outer diameter and 20 cm. in length which had been steam sterilized under pressure was poured 12 ml. of the sterilized aqueous solution as described above, which were then allowed to cool (freeze) at −50° C. for 1 hour. The upper cover of the mold was then removed, and the freeze molded material was subjected to partial dehydration under vacuum for 6 hours while avoiding thawing. Then, the vacuum was set off employing clean air which had been passed through a sterile filter, and the molded material (pipe) was removed from the mold. When the material was allowed to stand in a sterile room in which it was thawed. there was obtained a pipe weighing 7 g. (degree of dehydration, 40%; water content, 78% by weight), 5 mm. in inner diameter and 8 mm. in outer diameter. When the pipe was immersed in sterilized saline solution 0.9% by weight for 5 hours, there was obtained a hydrogel pipe weighing 10 g. (water content, 84% by weight), 5 mm. in inner diameter and 9 mm. in outer diameter.

The pipe was cut to two equal parts, and each part of the cut pipe was tied fast at one end by a knitted silk thread (JIS No. 1, 0.1 mm. in diameter, sterilized at 120° C. for 30 min.) which had been subjected to a dissolution treatment with sericin, to produce a cylinder (tiny test tubes) closed at the lower end.

Into each of the hydrogel test tube was poured 1 ml. of fresh blood (within 20 seconds after collection) from a goat (30 Kg.). After allowing to stand for 3 min., one of the test tubes was inclined repeatedly at an interval of 30 to 60 seconds nearly to disappearance of fluidity of the blood. The same procedures were applied to the other of the test tubes. The total period of time until no fluidity was observed when turned upside-down is taken as coagulation time.

Measurement of the coagulation time was made on two silicone test tubes (each 5 mm. in inner diameter) in the same way as above.

The in vitro coagulation time was 58 min. and 16 min. respectively with the hydrogel and silicone to find that the hydrogel of the present invention possessed an excellent anticoagulant activity compared to silicone which had been estimated favorably [cf. Tatsuzo Tanabe, Rinsho Geka, 22, 319 (1968)].

EXAMPLE 2

In 935 g. of water were dissolved 65 g. (water content, 8.5% by weight) of the same polyvinyl alcohol as used in Example 1 to give a 6% by weight solution. Into a polyethylene beaker (15 cm. in diameter at the bottom surface) were poured 170 g. of the aqueous solution, which was then subjected to steam sterilization at 120° C. for 30 min., followed by cooling at −50° C. for 2 hours (freeze molded), then immediately partial-dehydration for 6 hours was applied. There were obtained 97 g. (water content, 89% by weight; degree of dehydration, 43% by weight) of a white opaque elastic gel. The gel (ca. 8 mm. in thickness) was immersed in 100 ml. of physiological saline solution for 6 hours which had been steam sterilized. The gel was hydrated and weighed 143 g. (water content, 93% by weight; ca. 9 mm. in thickness). When it was applied with a load of 5 kg/cm$^2$, there were only 3 ml. of water exudated (outflux loss, 2%).

When the load was removed, the original form of the elastomer was recovered. Furthermore, tensile strength of the gel was found to be as high as 5 kg/cm$^2$.

From a piece of the sheet gel (disk, 15 cm. in diameter) was produced a Raschig ring 3 mm. in inner diameter, 3.5 mm. in outer diameter and 9 mm. in length employing a steam-sterilized punch. The ring was inserted into the cervical vein, exposed in asepsis under sodium thiopental anesthesia, controlling respiration through intubation, then the adventitia was loosened. A 5 mm. longitudinal incision was made with 1% xylocain dropping. The blood stream was temporarily stopped by ligation on both central and peripheral sides. Immediately the lumen of the vein was washed with sterilized physiological saline solution, and then the aboveprepared Raschig ring was inserted into the peripheral portion while avoiding damage of tunica intima. The ring was then moved to the central side so as to adjust the center of the ring at the incision line. The incised wound was closed with catgut (0.18 mm. in diameter) sterilized with ethylene oxide, then the blood stream was restored under the ligation of vessel at the center of the inserted Raschig ring.

Incision was made at the same position of the vein 3 weeks after, no imperforation of the ring was observed, although thin thrombosis was shown throughout the surface of the Raschig ring.

Comparisons were made with a silicone Raschig ring and a Teflon Raschig ring, respectively treated in the same way as above. Superior anticoagulant activity of the hydrogel of the invention was confirmed by observing remarkable thrombosis after 2 weeks in the latter experiments.

EXAMPLE 3

In 914 g. of water were dissolved 86 g. (water content, 7% by weight) of powdered polyvinyl alcohol available on the market (saponification value, 97 mol%; average degree of polymerization, 1,800; viscosity at 20° C. of the 4% aqueous solution, 28 cP) to give a 8.0% by weight solution.

Into a polyethylene beaker 7.2 cm in diameter at the bottom surface were poured 41 g. of the aqueous solution. Sterilization and freeze molding were applied in accordance with the procedures described in Example 1, followed by vacuum dehydration for 10 hours.

After thawing, there were obtained 8 g. of a white opaque gel (water content, 58% by weight; degree of dehydration, 80% by weight), which were immersed in 10 ml. of sterilized physiological saline solution for 6 hours. Consequently, the gel was hydrated and weighed 14 g. (water content, 76% by weight). Tensile strength of the gel (ca. 10 mm. in thickness) was as high as 5 kg/cm$^2$.

The disk thus obtained was folded in four just the same way as with a disk filter paper to form a conical vessel with no bottom.

Rabbit blood (10 ml.) was collected, and mixed with 1 ml. of 3.8% aqueous solution of sodium citrate, followed by addition of 10 ml. of 1/40M aqueous solution of calcium chloride. Into the above conical vessel were poured 3 ml. of the blood. When allowed to stand for 3 hours, there were observed almost no thrombosis.

A conical vessel was prepared from silicone disk, in which an experiment was carried out just the same way as above. Thrombosis appeared after 20 min. to demonstrate superiority of the hydrogel of the invention in anticoagulant activity.

EXAMPLE 4

In 89 g. of water were dissolved 13 g. of the same powdered polyvinyl alcohol as in Example 1 (water content, 8.5% by weight) to give 11.6% by weight aqueous solution. Into a mold for preparing 18 plates each 1 cm×1 cm×5 cm were poured 90 g. of the aqueous solution, which were then subjected to cooling at −53° C. for 1 hour (freeze molding). The mold was then dismantled, and the molded material was removed and promptly subjected to vacuum partial-dehydration for 6 hours. There were obtained 48 g. of a gel (water content, 78% by weight; degree of dehydration, 47% by weight). In a tensile test, the gel was not ruptured by a stress of 6 kg/cm$^2$. Thromogenosis experiment was carried out in the same way as in Example 3 with almost no thrombosis observed.

COMPARATIVE EXAMPLE 1

Into a square-shaped vessel 8 cm×8 cm in bottom surface were poured 41 g. of the same aqueous solution of polyvinyl alcohol as used in Example 2, which was then allowed to stand at ordinary temperature for 2 days. There was obtained a colorless, clear, soft and wet membrane. When the membrane was immersed in tap water for 6 hours, a portion of it was dissolved in water, and the membrane became sticky. There was not yielded a rubber-like gel at all as in Examples 1–4. This experiment shows that when an aqueous solution is simply dried, there is not obtained a rubber-like gel with a high water content according to the present invention.

COMPARATIVE EXAMPLE 2

Using a polyvinyl alcohol available on the market with saponification value of 78.5 mol%, average degree of polymerization of 1,800 and a viscosity at 20° C. of the 4% by weight of 36 cP in place of the polyvinyl alcohol used in Example 3, an experiment was carried out in the same way as in that example. There were obtained 7.4 g. (water content, 55% by weight) of a freeze molded and dehydrated mass. After thawing, the mass became soft even at 5° C., and a large amount of a viscous solution of polyvinyl alcohol was separated in layers in addition to a small amount of the gel layers.

This experiment shows that polyvinyl alcohol with a lower saponification value can not form a water-proof gel as in the present invention.

COMPARATIVE EXAMPLE 3

Using a polyvinyl alcohol available on the market with saponification value of 99.2 mol%, average degree of polymerization of 500 and viscosity at 20° C. of 4% aqueous solution of 5.6 cP in place of the polyvinyl alcohol used in Example 3, 20 g. of 18% by weight aqueous solution were freeze molded and dehydrated in the same way as in that example. There were yielded 13 g. (water content, 72% by weight) of an agar-like fragile gel with almost no elasticity observed. This experiment shows that polyvinyl alcohol of a lower degree of polymerization does not form a rubber-like elastic gel with a high mechanical strength as in the present invention.

EXAMPLE 5

A 6% by weight aqueous solution was prepared from polyvinyl alcohol used in Example 1, and 170 g. of aqueous solution were divided into 5 equal portions. Each of the portions was poured into polyethylene beaker (50 ml.) and cooled at −50° C. for 1 hour (freeze molded). The resulting mass was subjected to vacuum partial-dehydration respectively for 1–14 hours. Weight of the dehydrated gel after immersed in water for 6 hours was also measured.

| Evacuation (h.) | Dehydrated gel | | | Immersed gel | |
| --- | --- | --- | --- | --- | --- |
| | (g.) | Water content (% by weight) | Degree of dehydration (% by weight) | (g.) | Water content (% by weight) |
| 1 | 27 | 92 | 21 | 29 | 93 |
| 2 | 26 | 92 | 24 | 29 | 93 |
| 4 | 19 | 89 | 44 | 23 | 91 |
| 8 | 5 | 62 | 85 | 11 | 82 |
| 14 | 2.5 | 20 | 93 | 10 | 80 |

Tensile strength was measured also with the immersed gel.

| Evacuation time (h.) | Strength (kg/cm²) |
| --- | --- |
| 1 | 1 |
| 2 | 2 |
| 4 | 3 |
| 8 | 5 |
| 14 | 6 |

The present gel was associated with neither adhesion to each other nor deformation and remained unchanged in strength when allowed to stand in immersion in tap water for 90 days or longer.

A thromogenosis experiment was also carried out in the same way as in Example 3. There was almost no thrombosis observed.

COMPARATIVE EXPERIMENT 4

Concentration of the aqueous solution of polyvinyl alcohol with the same degree of polymerization as in Comparative Example 3, namely, of 500 was increased to 30% by weight. The aqueous solution weighing 160 g. was freeze molded at −73° C. for 1 hour, followed by vacuum partial-dehydration for 6 hours. The freeze molded and dehydrated mass weighing 106 g. (water content, 66% by weight) was thawed and then immersed in water for 8 hours. There took place hydration to a weight of 120 g. (water content, 70% by weight) with remarkable softening and partial deformation accompanied by dissolution into the water.

COMPARATIVE EXAMPLE 5

In Example 5, 34 g. of a 6% by weight aqueous solution of polyvinyl alcohol (saponification value, 99.4 mol%; average degree of polymerization, 2,600) were cooled (freeze molded), followed by allowing to stand at ordinary temperature for 1 hour. There was produced a sticky and soft gel (34 g.; degree of dehydration, 0%; water content, 94% by weight), which showed no elasticity and was broken at a tensile strength as low as 100 g/cm². When 10 g. of the gel were immersed in 30 ml. of water, deformation began to occur after ca. 20 hours, and the aqueous solution became turbid with the major portion of the gel left in sticky solution.

This experiment shows that when an aqueous solution of polyvinyl alcohol is subjected to freeze molding and thawing only, there is obtained a sticky gel with a low strength and insufficient water resistance. Unless a partial dehydration following the freeze molding is applied while avoiding thawing, strong and water resistant gel as in the present invention will not be produced.

COMPARATIVE EXAMPLE 6

To 90 g. of water were added 0.5 g. of the powdered polyvinyl alcohol used in Example 2 and 0.5 g. of carboxymethylcellulose. The mixture was boiled for 15 min. to a solution, which was cooled at room temperature, vigorously stirred and allowed to stand at −50° C. (frozen) for 10 hours, followed by prompt vacuum drying. There was obtained 1 g. of dried mass, which was a white sponge similar to but more fragile than foamed styrene and, in water, easily transformed to an adhesive solution.

This experiment shows that application of the procedures according to the present invention to an aqueous solution of polyvinyl alcohol at a concentration of about 0.5% produces a water-soluble freeze-dried mass.

EXAMPLE 6

The hydrogel pipe obtained in Example 1 (20 cm in length) was cut in a length of 4 cm. These were end-to-end anastomosed one to another respectively employing a knitted silk suture (JIS No. 1, 0.1 mm. in diameter, sterilized at 120° C. for 30 min.) which had been subjected to a dissolution treatment with sericin, a catgut (0.18 mm. in diameter, sterilized with ethylene oxide), Dexon ® suture (polyglycolic acid, 0.18 mm. in diameter, sterilized at 120° C. for 30 min.) and a taper cut needle. A suture test was run at a thread space of 1.5 mm. by the two-point support technique of suturing vascular graft (cf. Tatsuzo Tanabe, "Hogo Zairyo to Hogo, Fungo", p. 16, 61 and 91 (1979), Kanehara Shuppan; Tatsuzo Tanabe et al., "Jinko Kekkan", p. 56 and 84 (1977), Nanko-do).

It was found that the hydrogel pipe according to this invention was easily sutured with any kind of above-mentioned sutures with no rupture.

The hydrogel pipe was also tested for anticoagulant activity in the same way as in Example 2 with almost no thrombogenosis observed.

EXAMPLE 7

In 100 ml. of water were dissolved 23 g. of the powdered polyvinyl alcohol used in Example 2 (water content, 8.5% by weight) to give 17% by weight solution. The solution was subjected to steam sterilization under pressure (120° C.×30 min.) and cooled at the temperature of 40° C. In 20 g. of the resulting solution were dissolved 65,000 units (400 mg.) of powdered sodium heparin which had been sterilized with ethylene oxide gas. Twelve ml. of the mixed solution were poured into a mold in the same way as in Example 1, followed by the same procedures to give a pipe 5 mm. in inner diameter and 8 mm. in outer diameter weighing 8 g. (degree of dehydration, 34% by weight; water content, 75% by weight). The pipe was immersed in 0.9% by weight saline solution for 5 hours. There was obtained a hydrogel pipe 5 mm. in inner diameter and 9 mm. in outer diameter weighing 10 g. (water content, 80% by weight). The resulting pipe was cut in 0.5 cm. pieces. To 20 samples of the pieces (heparin content, 19,500 units) (5 g. of the total pieces) were added 20 ml. of 0.9% by weight saline solution. The mixture was allowed to stand for one day followed by separation of the aqueous phase from the pieces. The aqueous phase was tested for heparin by means of color reaction with toluidine. The procedures were repeated once a day with a fresh portion of the immersed solution (20 ml.). A clear toluidine color reaction (violet) was observed over a period of at least 28 days.

Separately a pipe (5 mm. in inner diameter, 8 mm. in outer diameter and 7 cm. in length) was prepared in the same way as above and tested for anticoagulant activity by the same method as in Example 2. There was observed almost no thrombosis.

EXAMPLE 8

The same procedures as in Example 7 were applied with an amount of heparin increased to 2 g. From the heparin-embedded hydrogel pipe (20 cm. in length) thus obtained was cut off a pipe 10 mm. in length, which was inserted into the inferior vena cava of a dog (12 kg.) and fixed with ligature. An incision was made after 118 days of blood circulation, and the heparin-embedded hydrogel pipe was removed. There was no thrombosis observed.

EXAMPLE 9

In 935 g. of water were dissolved 65 g. (water content, 8% by weight) of powdered polyvinyl alcohol available on the market (saponification value, 99.4 mol%; average degree of polymerization, 2,600; viscosity (20° C.) of the 4% by weight aqueous solution, 66 cP) to give a 6% by weight aqueous solution. Into a polyethylene beaker (8 cm. in diameter at the bottom surface) were poured 170 g. of the aqueous solution, which was subjected to steam sterilization under pressure (120° C.×30 min.) followed by cooling (freeze molding) at −50° C. for 0.7 hour. The freeze-molded material was then subjected to partial dehydration under vacuum for 6 hours while avoiding thawing. Then, the vacuum was set off employing clean air which had been passed through a sterile filter, and the molded material (disk) was removed. The material was allowed to stand in a sterile room in which it thawed to give white opaque elastic gel weighing 97 g. (water content, 89% by weight; degree of dehydration, 43% by weight). The gel (ca. 2 cm. in thickness) was immersed in 100 ml. of a synthetic humor (pH 8; 0.7% by weight of sodium chloride, 0.2% by weight of potassium chloride, 2.4% by weight of sodium hydrogen carbonate and 0.35% by weight of sodium dihydrogen phosphate; sterilized at 120° C. for 30 min.) for 6 hours. The gel was then hydrated to a weight of 143 g. (water content, 93% by weight). When the resulting gel was applied with a load of 4 kg/cm$^2$, there were only 3 ml. of water exudated (outflux loss, 2%). When the load was removed, the original form of the elastomer was restored. Furthermore, tensile strength of the hydrogel was found to be as high as 10 kg/cm$^2$.

From the hydrogel disk was cut off a piece 20 mm×13 mm×5 mm in size, which was used as a specimen for in vivo implantation.

The dorsal hair of a rabbit (2.5 kg) was shaved, and 0.5% ethyl alcohol solution of chlorhexidine was applied to the shaved area. After a further sterilization with 70% ethyl alcohol, a skin incision of 1.5 cm. in length was made, the above-mentioned piece was implanted, and the skin was sutured. Care was made so as not to position the incision line over the implanted specimen. After 24 hours, rubefaction and slight oncoides were observed, and under palpation the implanted piece was labile within the detached area of the subcutaneous tissue. After 4 days, the oncoides and rubefaction disappeared, and the suture was removed after 6 days. After 9 days, the palpable piece was fixed without migration. There was no local sign above the implanted site and no constitutional symptom at all after one month. The specimen with the subcutaneous tissue was extracted after 35 days, when the specimen was encapsuled with sheath. These were not mutually adhesive, but closely contacted. When the capsule was treated with 10% formalin, embedded in paraffin, and with hematoxylin and eosin stain, then with van Gieson's stain, there were observed very slight cellular infiltration and almost no inflammation, though a small number of pseudocidocytes and round cells were detected.

On the other hand, a strong foreign body reaction was observed around the removed catgut suture. For comparison's sake, a sponge 20 mm×13 mm×5 mm in size was implanted subcutaneously in antroposterior tissue of a rabbit. Disappearance of the rubefaction and the oncoides required 14 days, and the size of the sponge when extracted after a month was diminished by about 10% with strong cellular infiltration and a large number of foreign body giant cells observed which were indicative of foreign body tumorigenesis. A similar test was made with polymethylmethacrylate, in which disappearance of the rubefaction and the oncoides required a week with remarkable infiltration observed. It was therefore demonstrated that the hydrogel of the invention was far superior in biocompatibility.

EXAMPLE 10

In 914 g. of water were dissolved 86 g. (water content, 7% by weight) of polyvinyl alcohol available on the market (saponification value, 97 mol%; average degree of polymerization, 1,800; viscosity (20° C.) of the 4% aqueous solution, 28 cP) to give a 8.0% by weight solution.

Fourty-one grams of the aqueous solution were subjected to sterilization, freeze molding and vacuum partial-dehydration for 3 hours in the same way as in Example 9.

After thawing, there were obtained 35 g. (water content, 9% by weight; degree of dehydration, 15% by weight) of a white opaque gel. The gel was immersed in 10 ml. of sterilized physiological saline solution for 6 hours and hydrated to a weight of 37 g. (water content, 91% by weight). When the resulting gel (0.7 cm. in thickness) was applied with a load of 4 kg/cm$^2$, there was almost no exudation of water observed (water retentivity, 99%).

From the hydrogel disk was prepared a small test disk for implantation 13 mm. in diameter and 1.5 mm. in thickness. A longitudinal incision 3 cm. in length was made on the medial knee joint of a rabbit (2.5 kg.), then the medial muscle quadriceps femoris was incised longitudinally. The patella was then laterally dislocated, and the knee joint was flexed to resect the adipose tissue on the anterior surface of the joint. After cutting the crossed ligament, the joint capsule except the posterior one and the meniscus were resected. Then, the femoral articular cartilage was resected, the above-prepared implant was inserted and fixed on the femoral articular surface. The knee joint was fixed at an angle of 150° by applying plaster bandage from the superior femoral region to the foot. When the bandage was removed after 3 weeks, there was slight swelling observed at the joint. However, there was neither rubefaction nor local pyretogenesis. Primary coaptation was acceptable, and no exudate was observed. The knee joint was flexed at 120°, and protected limping gait was observed. Knee joint was moved from 150° to 90°. When specimen was treated with formalin, embedded in paraffin, then treated with hematoxylin and eosin stain, then with Mallory's azan stain, and microscopically examined, it was found that the surface of the formed femoral joint was encapsuled with connective tissue, and there was neither reactive ossein hypoplasia nor inflammation in medullary space.

On the other hand, when a comparison test was run with polymethylmethacrylate 1.5 mm. in thickness in the same way as above, there were observed after 3 weeks swelling at the joint, local pyrexia and rubefaction in superior patella region. After removal of the plaster bandage, the knee joint was moved slightly but its motility was not observed. There were also observed cellular infiltration and fibrous cicatrization. These findings indicate that the hydrogel of the invention is superior in biocompatibility.

EXAMPLE 11

In 914 g. of water were dissolved 86 g. (water content, 7% by weight) of powdered polyvinyl alcohol available on the market (saponification value, 97 mol%; average degree of polymerization, 1,800; viscosity (20° C.) of the 4% aqueous solution, 28 cP) to give a 8.0% by weight solution.

Fourty-one grams of the aqueous solution were subjected to sterilization, freeze molding and then vacuum partial-dehydration for 10 hours.

After thawing, there were obtained 8 g. (water content, 58% by weight; degree of dehydration, 80% by weight) of a white opague gel. The gel was immersed in 10 ml. of sterilized physiological saline solution for 6 hours and hydrated to a weight of 14 g. (water content, 76% by weight). When the resulting gel (0.5 cm. in thickness) was applied with a load of 4 kg/cm$^2$, there was almost no exudate (water retentivity, 99%).

From the gel was prepared a small test disk for implantation 13 mm. in diameter and 1.5 mm. in thickness. A longitudinal incision 3 cm. in length on the medial knee joint of a rabbit (2.5 kg.) and a longitudinal incision on the medial muscle quadriceps femoris were made. The patella was then dislocated laterally, and the knee joint was flexed to resect the adipose tissue of the anterior surface. After cutting the crossed ligament, the joint capsule except the posterior one and the meniscus were resected. Then, the femoral articular cartilage was resected, and in place of the resected cartilage, the above implant was inserted and fixed on the surface of the femoral surface. The knee joint was fixed at an angle of 150° by applying plaster bandage from the superior femoral region to the foot. When the bandage was removed after 3 weeks, there was slight swelling observed at the joint. However, there was neither rubefaction nor local pyrexia. Primary coaptation was acceptable, and no exudate was observed. The knee joint was flexed at an angle of 120°, and protected limping gait was observed. Knee joint was moved from 150° to 90°. When a specimen was treated with formalin, embedded in paraffin, then treated with hematoxylin and eosin, subjected to the Mallory's stain and microscopically examined, it was found that the surface of the formed femoral joint was encapsulated with connective tissue, and there was neither reactive ossein hypoplasia nor inflammation in medullary space.

On the other hand, when a comparison test was run with polymethylmethacrylate resin 1.5 mm. in thickness in the same way as above, there were observed after 3 weeks swelling at the joint, local pyrexia and rubefaction in the patella region. After removal of the plaster bandage, the knee joint was moved slightly but its motility was not observed. There was also observed inflammatory cellular infiltration and fibrous cicatrization. These findings indicate that the hydrogel of the invention is superior in biocompatibility.

EXAMPLE 12

In 89 g. of water were dissolved 13 g. of the same powdered polyvinyl alcohol as used in Example 10 (water content, 8.5% by weight) to give an 11.6% by weight solution. Into a mold for preparing 18 plates each 1 cm×1 cm×5 cm were poured 90 g. of the solution, which were then subjected to cooling at −53° C. for 1 hour (freeze molding). The molding was then dismantled, and the molded material was removed and promptly subjected to vacuum partial-dehydration for 6 hours. There were obtained 48 g. of a gel (water content, 78% by weight; degree of dehydration, 47% by weight). In a tensile test, the gel was not ruptured by a stress of 6 kg/cm$^2$. An implantation test was run with the gel in the same way as in Example 10. It was found that it was good in biocompatibility.

EXAMPLE 13

An aqueous solution of 6% by weight was prepared from the powdered polyvinyl alcohol used in Example 10, and 170 g. of the aqueous solution were divided into 5 equal portions. Each of the portions was poured into a polyethylene beaker (50 ml.) and cooled at −50° C. for 1 hour (freeze molded). The resulting mass was subjected to vacuum partial-dehydration respectively for 1–14 hours. Weight of the dehydrated gel after immersed in water for 6 hours was also measured.

| Evacuation time (h.) | Dehydrated gel | | | Immersed gel | |
|---|---|---|---|---|---|
| | (g.) | Water content (% by weight) | Degree of dehydration (% by weight) | (g.) | Water content (% by weight) |
| 1 | 27 | 92 | 21 | 29 | 93 |
| 2 | 26 | 92 | 24 | 29 | 93 |
| 4 | 19 | 89 | 44 | 23 | 91 |
| 8 | 5 | 62 | 85 | 11 | 82 |
| 14 | 2.5 | 20 | 93 | 10 | 80 |

Tensile strength was measured also with the immersed gel.

| Evacuation time (hr.) | Strength (at cut, kg/cm$^2$) |
|---|---|
| 1 | 1 |
| 2 | 2 |
| 4 | 3 |
| 8 | 5 |
| 14 | 6 |

The present gel was associated with neither adhesion to each other nor deformation, and remained unaltered in strength when allowed to immerse in tap water for 90 days or longer. An implantation test was run respectively with these gels in the same way as in Example 10. It was found that they were acceptable in biocompatibility.

EXAMPLE 14

In 140 ml. of water were dissolved 23 g. of the powdered polyvinyl alcohol used in Example 9 (water content, 8% by weight) to give a 13% by weight aqueous solution. The solution was subjected to steam sterilization under pressure (120° C.×20 min.).

Into a pipe mold 5 mm. in inner diameter, 10 mm. in outer diameter and 20 cm. in length which had been steam sterilized under pressure was poured 12 ml. of the aqueous solution, which were then allowed to cool (freeze) at −50° C. for 1 hour. The upper cover of the mold was then removed, and the freezed molded mass was subjected to partial-dehydration under vacuum for 6 hours while avoiding thawing. Then, the vacuum was set off employing clean air which had been passed through a sterile filter, and the molded pipe was removed. When the pipe was allowed to stand in a sterile room in which it was molten, there was obtained a pipe weighing 7 g. (degree of dehydration, 40%; water content, 78% by weight), 5 mm. in inner diameter and 8 mm. in outer diameter. When the pipe was immersed in sterilized saline solution 0.9% by weight for 5 hours, a hydrogel pipe weighing 10 g. (water content, 84% by weight), 5 mm. in inner diameter and 9 mm. in outer diameter was obtained.

The resulting pipe was cut in a length of 4 cm. These pieces were anastomosed one to another respectively employing a knitted silk thread (JIS No. 1, 0.1 mm. in diameter, sterilized at 120° C. for 30 min.) which had been subjected to a dissolution treatment with sericin, a catgut (0.18 mm. in diameter, sterilized with ethylene oxide), a Dexon ® suture (polyglycolic acid suture, 0.18 mm. in diameter, sterilized at 120° C. for 30 min.) and a taper cut needle. A suture test was run at a thread space of 1.5 mm. by the two-point support technique (cf. Tatsuzo Tanabe et al., "Jinko Kekkan" (1977), p.56 and 84, Nanko-do; Tatsuzo Tanabe, "Hogo Zairyo to Hogo, Fungo" (1979), p. 16, 61 and 91, Kanehara Shuppan).

It was found that the hydrogel pipe according to this invention was easily sutured with any of the abovementioned sutures and satisfactorily resistant to the operation. An implantation test was run with this hydrogel pipe in the same way as in Example 10. It was found that it was acceptable in biocompatibility.

EXAMPLE 15

A piece of a hydrogel (20 mm×13 mm×5 mm) obtained by the same procedures as in Example 1 was used as a test material for implantation.

Under intravenous injection of sodium pentbarbiturate, the loin hair of a rabbit was shaved, the skin incision and fasciotomy of 1.5 cm in length were made parallel to spine. An incision was then made on the exposed caro in the direction of muscle fibers. While opening the incision by a levator, the above hydrogel was inserted. The skin was sutured and applied with sterile collodium.

Specimens excised one month after the operation were examined grossly as well as microscopically with hematoxylin and eosin staining. There was observed in the specimens none of deformation, swelling, discoloration and syncretion. No cellular infiltration was also observed. There was no inflammatory reaction.

COMPARATIVE EXAMPLE 7

In 870 g. of water were dissolved 130 g. (water content, 8% by weight) of powdered polyvinyl alcohol available on the market (saponification value, 99.9 mol%; average degree of polymerization, 1,500; viscosity (20° C.) of the 4% aqueous solution, 25 cP) to give 12% by weight solution. On a glass were applied 2 g. of the aqueous solution by an applicator to a thickness of 0.3 mm. From the polyvinyl alcohol film (10 cm×13 cm×30 μm) air dried overnight was collected a cut piece 20 mm×13 mm in size, which was used as implant.

An incision was made in the same way as in Example 14 on the loin of a rabbit, in which the above-prepared polyvinyl alcohol film (a known polyvinyl alcohol film different from the polyvinyl alcohol gel of the invention, 0.5 cm×0.5 cm×0.03 mm). The specimens collected one month after were examined in the same way as above. There were observed globoid cells and giant cells around the implant. In addition, the prosthesis itself was much swelled and bloody.

EXAMPLE 16

An aqueous solution of 50% by weight of propylene glycol and 47% by weight of polyvinyl alcohol was prepared by mixing 500 g. of 9.4% by weight aqueous solution of polyvinyl alcohol having saponification value of 99.5 mol%, degree of polymerization of 2,600 and a viscosity (20° C.) of the 4% aqueous solution of 67 cP and 500 g. of propylene glycol. The aqueous solution was steam sterilized under pressure at 120° C. for 30 min. and allowed to cool in a sterile room.

Fourty-one grams of the resulting aqueous solution were poured onto a polyethylene projection plate (projection height, 1 mm.; projection density, 74,000/m$^2$; projection shape, cylinder 1.8 mm. in diameter; area occupied by the total of the projections, 20%; projection plate, 48 cm×17 cm) and evenly applied by a spatula (application, 0.7 mm in thickness). The applied plate was cooled at −50° C. for 0.7 hour (cold mold solidification) and then partially under vacuum for 4 hours. There was obtained a white opaque gel (net) weighing 24.6 g. (degree of dehydration, that is, percent decrease in weight of the cooled and solidified mass, 40% by weight). Apparent tensile strength of the net was as high as 1 kg/cm$^2$. It possessed devil's tongue jelly-like elasticity and flexibility and the stronger mechanical strength than that of devil's tongue jelly with a compressive strength of 10 kg/cm$^2$ or higher.

The film (perforated plate gel) had openings each 1.8 mm. in diameter, percent perforation (ratio of the area) of 20% and a thickness of approximately 0.5 mm. It was placed and enclosed in a polyethylene bag (50 cm×20 cm) which had been sterilized with propylene oxide.

An adult mongrel dog weighing 11 kg. under intravenous injection of sodium pentobarbiturate and oxygen supply by means of an endotracheal tube was subjected to an incision at the ninth intercostal space of the left chest to expose the left leaf of the diaphragm, an approximately 80% portion of which was then excised. The excised portion was repaired by the above-prepared hydrogel film (7 cm×7 cm×0.5 mm) which was sutured with silk. Penicillin was administered during a week. Fluoroscopic and X-ray examination made one year after the operation indicated that the repaired diaphragm worked well with no elevation observed in comparison with the right leaf of the diaphragm. Specimens collected from the sacrified body were examined grossly and histologically to find that the hydrogel membrane was positioned between the abdominal viscera and the lungs, and encapsuled with thin fibrous tissue. There was neither granulation nor foreign body reaction observed.

EXAMPLE 17 in 4,800 g. of water were dissolved 630 g. (water content, 7% by weight) of polyvinyl alcohol having saponification value of 97.5 mol%, average degree of polymerization of 2,200 and viscosity (20° C.) of the 4% aqueous solution of 56 cP to give 11.4% by weight solution.

An aqueous solution of 7.4% by weight of polyvinyl alcohol and 35% by weight of glycerin was prepared by mixing 4,536 g. of the above aqueous solution and 2,443 g. of glycerin. The aqueous solution was steam sterilized under pressure at 120° C. for 30 min. and allowed to stand in a sterile room.

Twenty-nine grams of the resulting aqueous solution were poured onto a stainless steel projection plate (projection height, 0.25 mm.; projection density, 74,000/m$^2$; projection shape, cylinder 1.8 mm. in diameter; area occupied by the total of the projections, 20%; projection plate, 48 cm×27 cm) and evenly applied by means of an aluminum plate (27 cm×4 cm×0.1 cm) to a film thickness of 0.25 mm. The applied plate was cooled at −60° C. for 0.7 hour (cold mold solidification) and then partially dehydrated under vacuum for 5 hours. There was obtained a white opaque gel weighing 19 g. (degree of dehydration, 33% by weight). Apparent tensile strength of the net was as high as 2 kg/cm$^2$. The film (perforated plate gel) had openings each 1.8 mm. in diameter, a percent perforation (ratio of the area) of 20% and a thickness of 0.2 mm. It was placed and enclosed in a polyethylene bag (50 cm×30 cm) which had been sterilized with propylene oxide.

Under intravenous sodium pentobarbiturate anesthesia, the hair was shaved in the Achilles' tendon region, and a longitudinal skin incision 1.5 cm. in length was made to expose the paratenon. An incision of the anterior paratenon and tendon 5 mm. in length was made along fibrous tissue. Supporting the incised region with a levator, the tendon was pressed and rubbed up and down from side to side. Thereafter, the above-prepared hydrogel film (0.3 cm×0.5 cm×0.02 cm) was inserted into the region of the incision, and the anterior paratenon and the tendon were sutured with a stitch. After skin suture, sterilized collodium was applied. Nearly comfortable jumping was observed postoperatively, and all of the function became normal after 3 days. One month later, the Achilles' tendon region was excised and examined microscopically after hematoxylin and eosin staining. There was neither giant cell nor cellular infiltration observed around the tendon and hydrogel. Regeneration of the blood vessel and formation of the lumen were also acceptable.

COMPARATIVE EXAMPLE 8

A polyvinyl alcohol film prepared in accordance with the method in Comparative Example 7 (a prior art polyvinyl alcohol film different from the hydrogel of the invention)(0.3 cm×0.5 cm×0.02 cm) was inserted into the incised region of the Achilles' tendon of a rabbit in the same way as in Example 17. When the specimens obtained one month after the operation were examined, the test material was much swelled with no original form left, and giant cells were observed around the implant. Marked cellular infiltration was observed, the hydrogels were scattered and the intercellular material in the connective tissue was hardly stainable. Tendon fibers lines were disturbed by connective tissue.

EXAMPLE 18

A mixed aqueous solution of polyvinyl alcohol and glycerin obtained in the same way as in Example 17 was applied to a sterilized glass plate by means of an applicator to a thickness of 0.3 mm. The applied plate was subjected to solidification (−30° C.) and the vacuum partial-dehydration (degree of dehydration, 35% by weight) according to the present invention to produce a hydrogel film (2 cm×2.3 cm, 0.2 mm. in thickness), which was used as an implant. Under intravenous sodium thiopental anesthesia, the hair was shaved on the scalp of an adult mongrel dog weighing 17 kg., and a longitudinal scalp incision 7 cm. in length was made in the right parietal region. The temporal muscle was stripped off, and then the parietal bone was bored by means of a drill. A bone defect of chicken egg size was provided by means of a rongeur, and the dura mater 1.5 cm×2 cm was excised. To the excised region was applied the above-prepared hydrogel film, which was sutured at the four corners, followed by temporal muscle suture and scalp suture.

Six months after the operation, the hydrogel film, dura mater and brain were isolated from the sacrificed body, which were examined grossly and microscopically after hematoxylin and eosin stain. There was no adhesion observed between the hydrogel film and the brain surface. Whereas the surface of the hydrogel was encapsuled with theca, almost no adhesion to pia mater was observed. There was neither cellular infiltration nor hyperplasia of giant cells observed.

EXAMPLE 19

A mixture was prepared of 30 g. of powdered polyvinyl alcohol (saponification value, 99.5 mol%; average degree of polymerization, 2,600; viscosity (20° C.) of the 4% aqueous solution, 66 cP), 158 g. of sorbitol and 292 g. of water. The mixture was stirred at 90° C. for 2 hours, then subjected to steam sterilization under pressure (120° C.×30 min.) and allowed to stand in a sterile room. Crystalline potassium penicillin G (sterile dry powder) 20 mg. (33,000 units) were dissolved in the mixture to prepare an aqueous solution containing 50 ppm of the antibiotic, 5.8% by weight of polyvinyl alcohol and 33% by weight of sorbitol. Fourty-five grams of the aqueous solution were poured onto a polyurethane projection plate (projection height, 0.5 mm.; projection density, 74,000/m$^2$; projection shape, cylinder 1.8 mm. in diameter; area occupied by the total of the projections, 20%; projection plate, (100 cm×17 cm) and evenly applied by a spatula (application, 0.3 mm. in thickness). The applied plate was cooled at −58° C. for 0.7 hour (solidification and molding) and then partially dehydrated under vacuum for 4 hours. There was obtained a white opaque film (net) weighing 32 g. (degree of hydration, 30% by weight). Apparent tensile strength of the net was as high as 3 kg/cm$^2$. The net had openings each 1.8 mm. in diameter, a perforation rate of 20% and a thickness of approximately 0.2 mm. It was placed and enclosed in a polyethylene bag (100 cm×20 cm) which had been sterilized with propylene oxide.

An adult mongrel dog weighing 13 Kg. was thoractomized under intravenous sodium pentobarbiturate anesthesia. The left pericadium was excised to such a large extent that only a margin to suture was left. The resected region was repaired employing the above-prepared hydrogel film (5 cm×5 cm×0.2 mm).

Six months after the operation, a preparation from the anaplerotic region of the sacrificed body was examined grossly, microscopically and scanning electron microscopically. There was no adhesion between the heart and the anaplerotic region observed. The hydrogel surface was encapsuled with endothelial tissue and was smooth. Histopathological examination revealed no cellular reaction, and thin endothelial tissue was found on the heart side.

EXAMPLE 20

An adult mongrel dog weighing 15 kg. was subjected to thoracotomy in accordance with the method in Example 19 to produce a diaphragmatic defect. The defect was repaired with a hydrogel film (4 cm×6 cm×0.2 mm) prepared according to Example 19. A specimen obtained 6 months after the operation, was examined. No adhesion between the repaired region and the lungs was observed. As in the case of Example 19, there was encapsulation with thin fibrous tissue, and no tissue reaction was observed.

EXAMPLE 21

A hydrogel film (0.2 mm. in thickness, 1.3 cm×1.2 cm) according to the present invention was prepared in the same way as in Example 18.

Under intravenous sodium pentobarbital anesthesia, the knee joint of a rabbit weighing 2.5 kg. was made hairless, and a longitudinal incision 2 cm. was made followed by medial dislocation of the patella. An incision was made on soft tissue of the patella lateral border except the tendon. Tendon of extensor digitorum longus muscle was removed to open the knee joint. Intraarticular soft tissues such as articular capsule, crossed ligament and meniscus as well as the articular cartilage was excised by means of rongeur, periosteotome and scissors, and the articular face was polished by means of a raspatory. The above-prepared hydrogel film was inserted to cover the surface. After repositioning of patella, articular capsule and soft tissue were sutured. After skin suture, the joint was fixed in extension with plaster bandage. Specimens collected one month after the operation were examined grossly and microscopically with hematoxylin and eosin staining. None of swelling and inflammation was observed. The knee joint was at a flexure of 90°, and was moved at an angle between 160° and 70°. The articular surface was covered with connective tissue, and there was neither ossein proliferation nor inflammation of the lumen of bone marrow tunnel. The articular surface was similar to that of the healthy animal.

What is claimed is:

1. The process of preparing a product suitable for medical use composed of a water-insoluble hydrogel having a high water content which comprises preparing an aqueous solution containing not less than 6 weight percent of a polyvinyl alcohol having a degree of hydrolysis of not less than 97 mole percent and an average polymerization degree of not less than 1100, pouring said aqueous polyvinyl alcohol solution into a desired shape of a vessel or mold, freeze-molding said poured aqueous polyvinyl alcohol solution at a temperature below −5° C., and thereafter partially dehydrating the resultant molded product without appreciable thawing thereof to a dehydration percentage of not less than 5 weight percent.

2. The process of claim 1 wherein the polymerization degree of the polyvinyl alcohol is in the range of 1,800 to 2,600.

3. The process of claim 1 wherein the partial dehydration is carried out in a vacuum.

4. The process of claim 1 wherein the partially dehydrated molded product is thereafter thawed at about room temperature.

5. The process of claim 4 wherein the thawed product is subjected to a treatment with water or physiological saline so that the resultant product has a water content of from 45 to 95 weight percent.

6. The process of claim 1 wherein an antithrombotic agent is added to the aqueous polyvinyl alcohol solution.

7. The process of claim 6 wherein the antithrombotic agent is heparin.

8. The product according to the process of claim 1.

9. The product according to the process of claim 5.

10. The product according to the process of claim 6.

11. The product according to the process of claim 7.

* * * * *